United States Patent
Kuratomi et al.

(10) Patent No.: US 10,776,919 B2
(45) Date of Patent: Sep. 15, 2020

(54) X-RAY DIAGNOSTIC APPARATUS AND IMAGE PROCESSING APPARATUS TO SPECIFY A POSITION OF A PATHOLOGICAL ABNORMALITY CANDIDATE

(71) Applicant: Canon Medical Systems Corporation, Otawara-shi (JP)

(72) Inventors: Naoko Kuratomi, Sakura (JP); Yasushi Sakai, Kawasaki (JP); Yuuji Kuki, Utsunomiya (JP); Tomoaki Ogura, Otawara (JP)

(73) Assignee: Canon Medical Systems Corporation, Otawara-shi (JP)

( * ) Notice: Subject to any disclaimer, the term of this patent is extended or adjusted under 35 U.S.C. 154(b) by 133 days.

(21) Appl. No.: 15/966,011

(22) Filed: Apr. 30, 2018

(65) Prior Publication Data
US 2018/0322633 A1 Nov. 8, 2018

(30) Foreign Application Priority Data
May 2, 2017 (JP) ................... 2017-091512

(51) Int. Cl.
*G06T 7/73* (2017.01)
*A61B 6/03* (2006.01)
*G06T 7/00* (2017.01)
*G06T 11/00* (2006.01)
(Continued)

(52) U.S. Cl.
CPC .............. *G06T 7/0016* (2013.01); *A61B 6/03* (2013.01); *A61B 6/502* (2013.01); *A61B 6/52* (2013.01); *G06T 5/003* (2013.01); *G06T 5/008* (2013.01); *G06T 7/0012* (2013.01); *G06T 7/74* (2017.01); *G06T 11/001* (2013.01); *G06T 2200/24* (2013.01); *G06T 2207/10081* (2013.01); *G06T 2207/10112* (2013.01); *G06T 2207/10116* (2013.01); *G06T 2207/20104* (2013.01);
(Continued)

(58) Field of Classification Search
None
See application file for complete search history.

(56) References Cited

U.S. PATENT DOCUMENTS 6,714,320 B1 * 3/2004 Nakahara ............. H04N 1/4051
358/3.12
7,630,533 B2 * 12/2009 Ruth .................... G06K 9/4638
382/131
(Continued)

FOREIGN PATENT DOCUMENTS

JP 2015-177928 10/2015

*Primary Examiner* — Tahmina N Ansari
(74) *Attorney, Agent, or Firm* — Oblon, McClelland, Maier & Neustadt, L.L.P.

(57) ABSTRACT

According to one embodiment, an X-ray diagnostic apparatus includes processing circuitry. The processing circuitry is configured to specify a position of a pathological abnormality candidate and a pathological abnormality type of a breast of a subject from a plurality of pieces of tomographic images obtained by performing tomosynthesis imaging on the breast. The processing circuitry is configured to, in a two-dimensional image obtained by performing X-ray imaging on the breast, perform image processing on a position corresponding to the position of the specified pathological abnormality candidate in accordance with the pathological abnormality type.

14 Claims, 10 Drawing Sheets

(51) Int. Cl.
*A61B 6/00* (2006.01)
*G06T 5/00* (2006.01)
(52) U.S. Cl.
CPC ............. *G06T 2207/30068* (2013.01); *G06T 2207/30096* (2013.01)

(56) References Cited

U.S. PATENT DOCUMENTS

| | | | | |
|---|---|---|---|---|
| 7,664,604 | B1* | 2/2010 | Heine | G16H 50/30 |
| | | | | 702/19 |
| 10,448,912 | B2* | 10/2019 | Esashi | A61B 6/481 |
| 2010/0226475 | A1* | 9/2010 | Smith | A61B 6/502 |
| | | | | 378/37 |
| 2015/0269766 | A1 | 9/2015 | Kobayashi | |
| 2018/0322633 | A1* | 11/2018 | Kuratomi | G06T 5/003 |

* cited by examiner

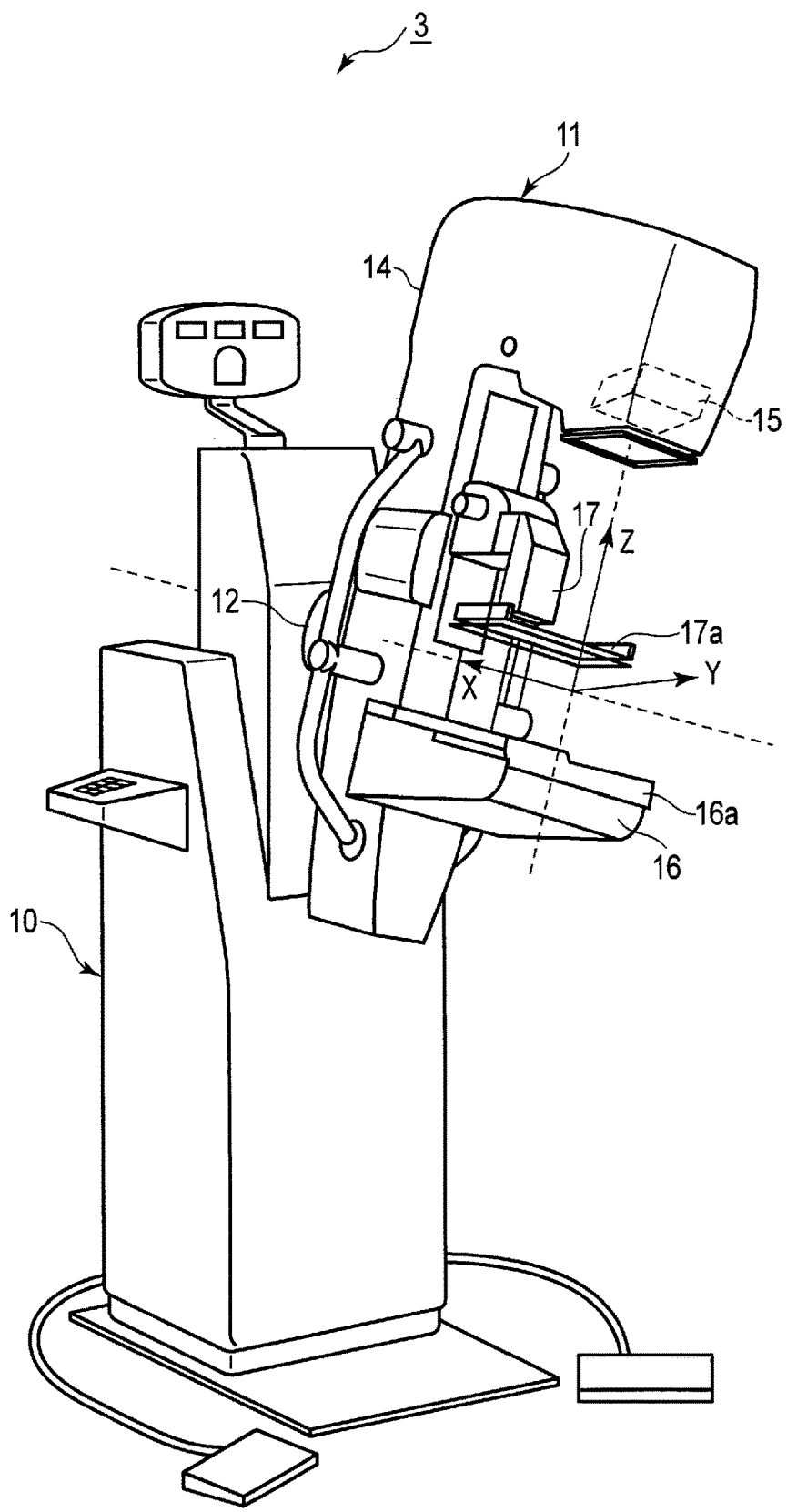
F I G. 2

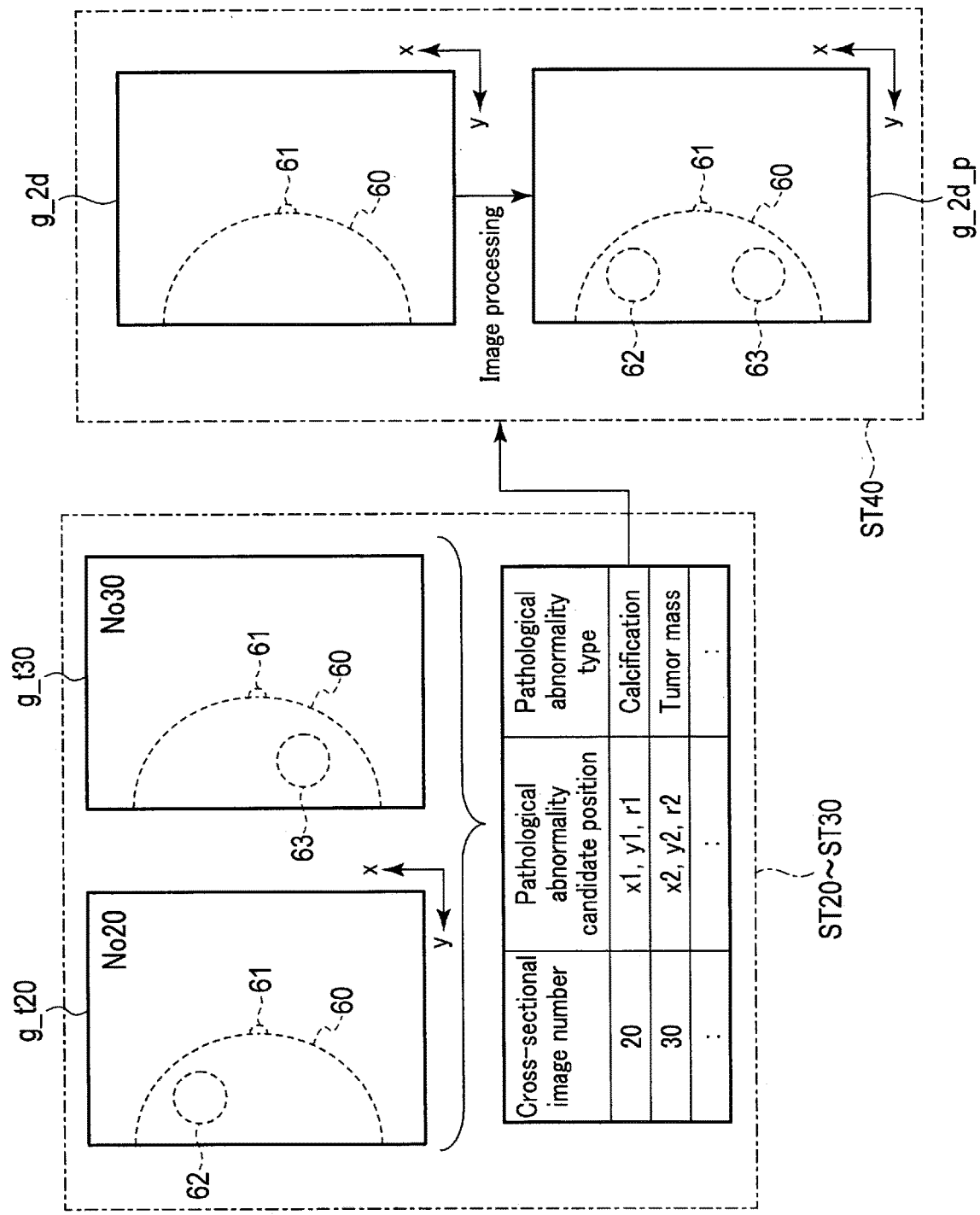
F I G. 5

X-RAY DIAGNOSTIC APPARATUS AND IMAGE PROCESSING APPARATUS TO SPECIFY A POSITION OF A PATHOLOGICAL ABNORMALITY CANDIDATE

CROSS-REFERENCE TO RELATED APPLICATIONS

This application is based upon and claims the benefit of priority from prior Japanese Patent Application No. 2017-91512, filed on May 2, 2017, the entire contents of which are incorporated herein by reference.

FIELD

Embodiments described herein relate generally to an X-ray diagnostic apparatus and an image processing apparatus.

BACKGROUND

A breast X-ray diagnostic apparatus is generally used for a mammography examination upon a breast cancer examination to perform X-ray imaging of a breast of a subject in a two-dimensional image. For many years, an X-ray diagnostic apparatus of this type has been using an analog film (hereinafter referred to as a film) for an image reception system. Furthermore, after performing the X-ray imaging, a two-dimensional image of a breast would be formed on the developed film. As an observation system of the two-dimensional image, an X-ray film illuminator would be used to present the two-dimensional image on a film by transmitting light from a back surface side to a front surface side of a hung film.

However, in recent years, advancement of technology regarding the X-ray diagnostic apparatus has caused changes in the reception system of the X-ray imaging and the observation system of the two-dimensional image. For example, the reception system of the X-ray imaging has been changed so as to use a digital detector such as a computed radiography (CR) or a flat panel detector (FPD) instead of a film. Along with this change, the observation system of the two-dimensional image has been changed so as to display image data obtained by the digital detector on a display such as a monitor instead of the X-ray film illuminator.

Furthermore, in addition to such changes in the reception system and the observation system, an imaging method carried out by the X-ray diagnostic apparatus and a breast cancer detection aiding technique have also made progress. Conventionally, as the imaging method carried out by the X-ray diagnostic apparatus, a system for obtaining a two-dimensional image of a breast of a subject has been used by arranging an X-ray source to perform imaging from a certain angle. In addition to this, recently, the imaging method uses a three-dimensional imaging method (hereinafter referred to as a tomosynthesis) that performs a three-dimensional reconstruction on images obtained by moving the X-ray source to perform imaging from a plurality of angles, and creates a plurality of pieces of tomographic images in accordance with a depth inside a breast. Since the tomosynthesis obtains a tomographic image per depth inside the breast, there is an advantage in that a region that has been difficult to diagnose because of overlapping mammary glands would become easier to observe.

On the other hand, as the breast cancer detection aiding technique, there is a mammography computer-aided detection (CAD) (hereinafter merely referred to as "CAD"). The CAD allows a region of a tumor mass or calcification, etc. that is characteristic of a breast cancer to be detected by computer analysis.

Normally, there is no particular problem with the X-ray diagnostic apparatus mentioned above; however, an inventor of the present invention considers that there is room for improvement in the following points. For example, since a display such as a monitor has a lower density resolution compared to a film, it is unable to sufficiently express thickness information of mammary glands or a pathological abnormality. Therefore, in the case of using a display, since the displayed two-dimensional image is difficult to be observed, there is room for improvement in this respect. This would cause inconvenience in that the diagnosis becomes difficult since a diagnostic reading doctor would find it difficult to determine whether a region of interest in the two-dimensional image indicates overlapping mammary glands or a pathological abnormality. From the perspective of solving such inconvenience, the aforementioned tomosynthesis is used. However, in the case of using the tomosynthesis, since numerous tomographic images are to be read, there is a greater burden on the diagnostic reading doctor, compared to when, conventionally, a piece of two-dimensional image was read; which, in this respect, there is room for improvement. Such respect also applies to a U.S. breast cancer examination work flow. In the U.S. breast cancer examination work flow, a subject receives a breast cancer examination at an image center, and a diagnostic reading doctor (A) at the image center reads all of the tomographic images and sends a report presenting a diagnostic reading result to a diagnostic reading doctor (B) who is a family doctor of the subject. The report includes a character string that describes the diagnostic reading result and a two-dimensional image. The diagnostic reading doctor (B) is not a specialist in diagnostic reading. The diagnostic reading doctor (B) displays the received report. Here, in the same manner as mentioned above, there is an inconvenience for the diagnostic reading doctor (B) in that the displayed two-dimensional image is difficult to observe. From the perspective of solving this inconvenience, even if the breast cancer examination work flow were to be changed to send to the diagnostic reading doctor (B) a plurality of tomographic images regarding the diagnostic reading result from among all of the tomographic images, it would be a great burden on the diagnostic reading doctor (B) because the diagnostic reading doctor (B) is not a diagnostic reading specialist, however, would have to confirm a plurality of tomographic images.

In other words, the conventional X-ray diagnostic apparatus can be improved to solve the points of difficulty in observing the displayed two-dimensional image in the case of using a display, and a great burden on both the diagnostic reading doctors (A) and (B) in the case of using the tomosynthesis.

The object of the present invention is to obtain an easily observable two-dimensional image when being displayed on a display, and to reduce the burden on a diagnostic reading doctor.

BRIEF DESCRIPTION OF THE DRAWINGS

FIG. 2 is a perspective view showing an outer appearance of an X-ray imaging apparatus of the embodiment.

FIG. 5 is a schematic view for explaining an operation of the present embodiment.

DETAILED DESCRIPTION

In general, according to one embodiment, an X-ray diagnostic apparatus includes processing circuitry.

The processing circuitry is configured to specify a position of a pathological abnormality candidate and a pathological abnormality type of a breast of a subject from a plurality of pieces of tomographic images obtained by performing tomosynthesis imaging on the breast.

The processing circuitry is configured to, in a two-dimensional image obtained by performing X-ray imaging on the breast, perform image processing on a position corresponding to the position of the specified pathological abnormality candidate in accordance with the pathological abnormality type.

Hereinafter, an embodiment will be explained with reference to the drawings.

Figure 1:
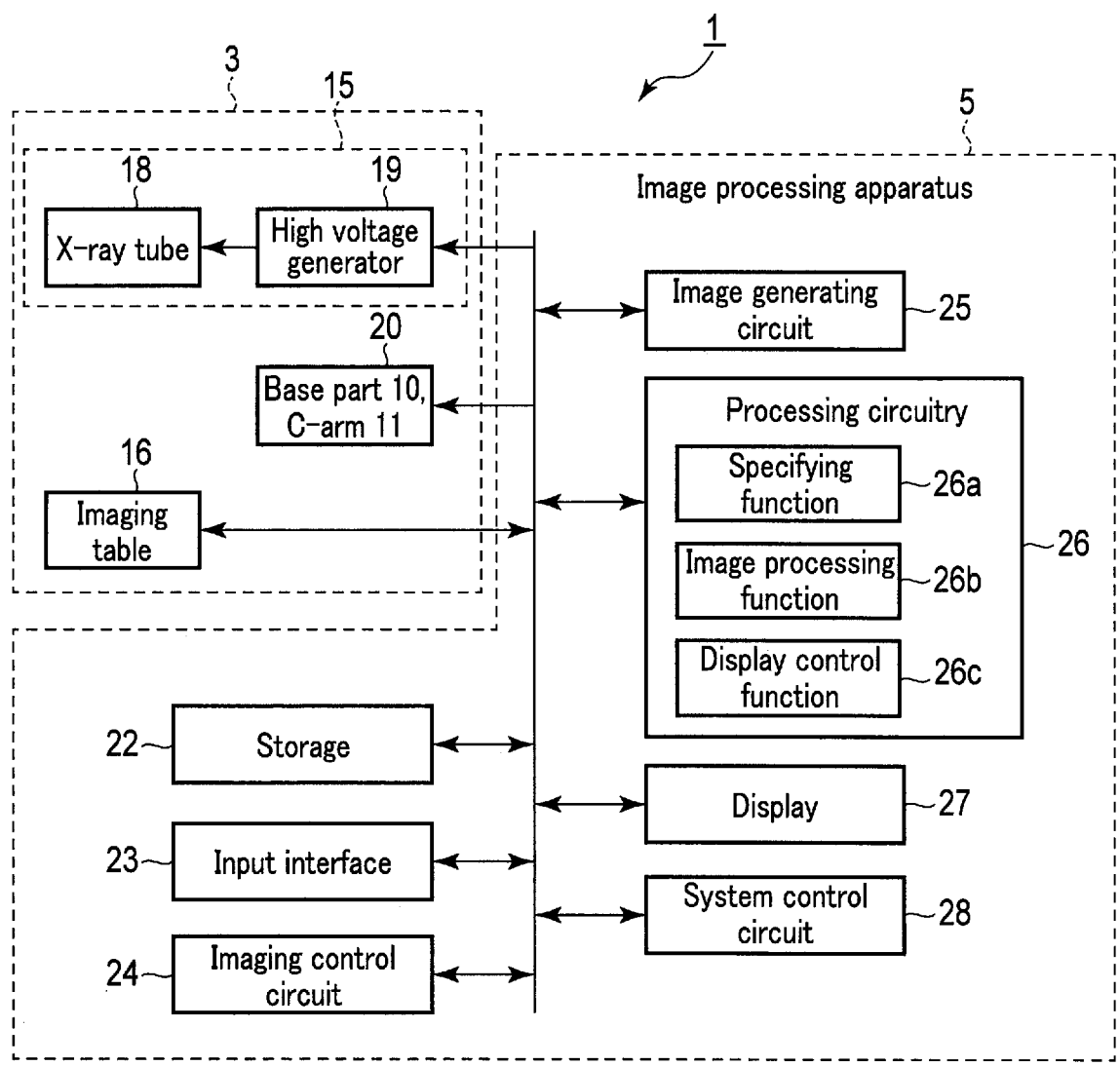
FIG. 1 is a block diagram showing a configuration of an X-ray diagnostic apparatus according to an embodiment.

FIG. 1 is a block diagram showing a configuration of an X-ray diagnostic apparatus according to the embodiment. FIG. 2 is a perspective view showing an outer appearance of an X-ray imaging apparatus. An X-ray diagnostic apparatus 1 comprises an X-ray imaging apparatus 3 and an image processing apparatus 5.

The X-ray imaging apparatus 3 comprises a base part 10 and a C-arm 11. The C-arm 11 is attached to an axial part 12 that is projected from the base part 10. In this manner, the C-arm 11 is rotatably supported on the base part 10 with an axial center of the axial part 12 as a rotation central x-axis. By rotating the C-arm 11, imaging such as CranioCaudal projection (CC), MedioLateral projection (ML), and MedioLateral Oblique projection (MLO) can be performed.

The C-arm 11 is configured by attaching an X-ray generator 15, an imaging table 16, and a compression unit 17 on an arm main body 14. The X-ray generator 15 and the imaging table 16 are arranged on both end parts of the arm main body 14. The compression unit 17 is arranged in between the X-ray generator 15 and the imaging table 16.

The X-ray generator 15 comprises an X-ray tube 18 and a high voltage generator 19. When a tube voltage is applied and a filament current is supplied from the high voltage generator 19, the X-ray tube 18 generates an X-ray during a predetermined X-ray continuation time towards a compression unit. The tube voltage to be applied and the X-ray continuation time are adjusted to a value that is suitable for imaging by receiving a control signal from an imaging control circuit 24.

The X-ray tube 18 comprises a cathode filament and an anode. The anode is an Mo anode that is made of Mo (molybdenum), an Rh anode that is made of Rh (rhodium), an Mo/Rh anode that is made of a mixture of Mo and Rh, and a W anode that is made of W (tungsten). These anodes are switchable as needed by receiving a control signal from the imaging control circuit 24.

The cathode filament that has received the filament current supply is heated and generates thermoelectrons. The thermoelectrons that have been generated are collided against the anode by the tube voltage applied between the cathode filament and the anode. In this manner, an X-ray is generated by colliding the thermoelectrons against the anode. The thermoelectrons that collide against the anode causes a tube current to flow. The tube current is adjusted by the filament current. An X-ray radiation dose upon imaging is adjusted by receiving a control signal from the imaging control circuit 24, and adjusting a tube current-time lapse product, which is a product of the tube current and the X-ray continuation time.

On the X-ray tube 18 is attached a radiation quality filter for changing a radiation quality of the generated X-ray. The radiation quality filter is an Mo filter that is made of Mo, an Rh filter that is made of Rh, an Al filter that is made of Al (aluminum), an Ag filter that is made of Ag (silver), or a filter made of a combination thereof, etc. These radiation quality filters are switchable as needed by receiving a control signal from the imaging control circuit 24.

The compression unit 17 includes a compression plate 17a that is supported by the C-arm 11 in a manner that can change distances along a mounting surface 16a of the imaging table 16. The compression unit 17 receives the control signal from the imaging control circuit 24, compresses a breast of a subject against the mounting surface 16a by operating the compression plate 17a, and brings a breast thickness to a predetermined state.

The imaging table 16 is a unit that accommodates in a chassis the digital detector, such as a flat panel detector (FPD) that detects an X-ray transmitted through the breast. The imaging table 16 is supported by the C-arm 11 so as to become close to/distant from the X-ray tube 18 along a Z-axis that joins a surface center of the mounting surface table 16a and a focal point of the X-ray tube 18. Here, a Y-axis is defined as an axis that is orthogonal to an X-axis and the Z-axis. In other words, an XYZ coordinate system is a rotating system of coordinates that has the X-axis as the rotation central axis. The Z-axis is an axis that defines a thickness direction of the breast, and an XY-plane is an axis that defines a spreading direction perpendicular to the thickness direction of the breast.

Furthermore, in the case where the compression unit 17 comprises an upper side compression plate and a lower side compression plate, and a magnification imaging is performed by separating a distance between the mounting surface 16a and the breast that is compressed between the upper side compression plate and the lower side compression plate, a magnifying ratio may be set to a suitable state for imaging by changing the chassis of the imaging table 16 to that for the magnification imaging.

The digital detector inside the imaging table 16 includes a plurality of semiconductor detection elements of a direct conversion system or an indirect conversion system. The direct conversion system converts an incident X-ray directly into an electrical signal, and the indirect conversion system converts the incident X-ray into a light by a fluorescent substance, then converts the light into an electrical signal. These semiconductor detection elements are arranged in a two-dimensional lattice form. The digital detector also includes an amplifier circuit and an A/D conversion circuit in addition to the semiconductor detection elements of a photo-diode, etc. This allows a signal charge generated at a plurality of semiconductor detection elements along with the X-ray incidence to be output to the image processing apparatus 5 as a digital signal via the amplifier circuit and the A/D conversion circuit.

Together with the X-ray imaging apparatus 3, the image processing apparatus 5 comprises a storage 22, an input interface 23, an imaging control circuit 24, an image generating circuit 25, processing circuitry 26, a display 27, and a system control circuit 28.

Figure 3:
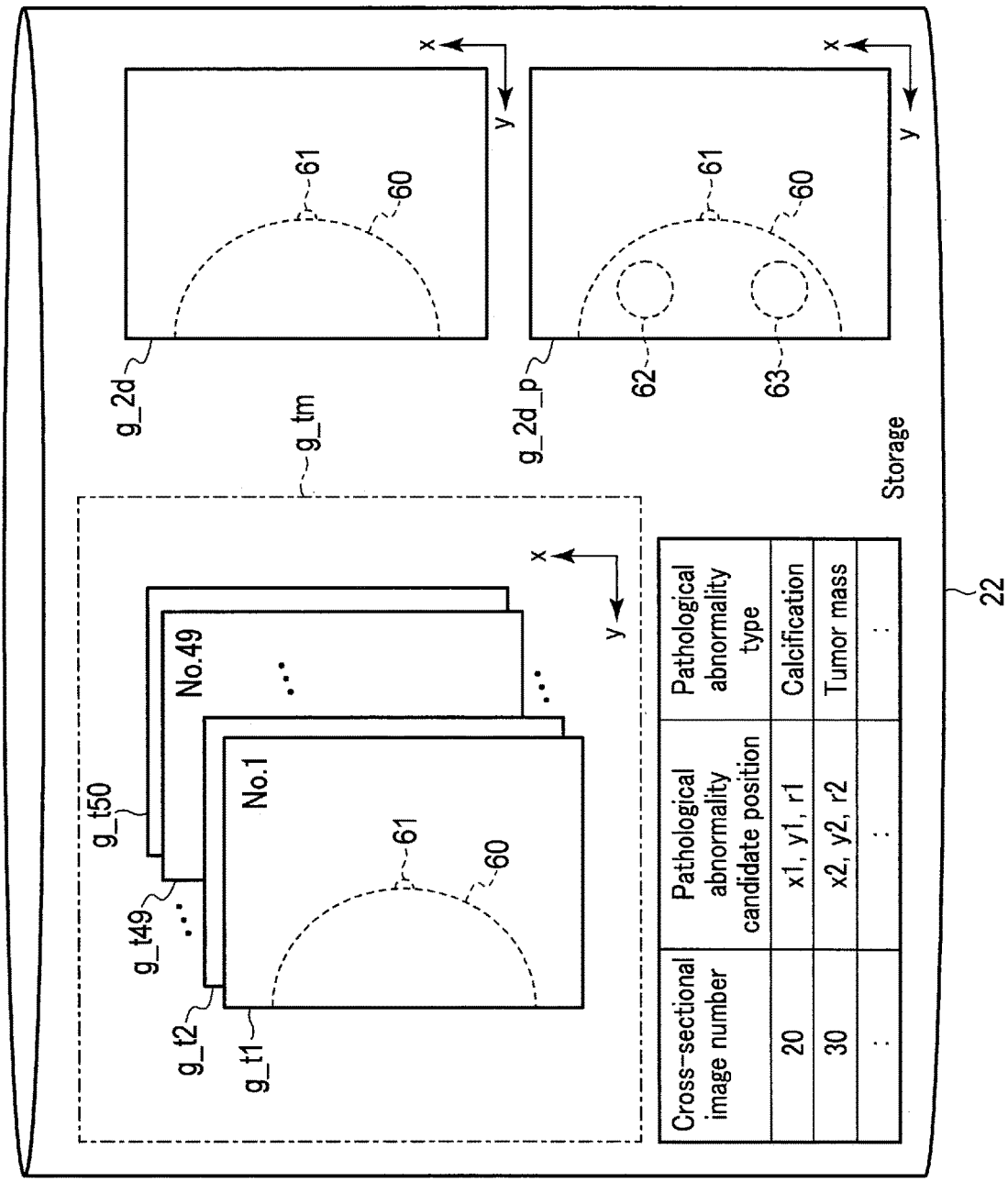
FIG. 3 is a schematic view for explaining a storage of the embodiment.

The storage 22 is comprised of a memory that records electric information, such as a Read Only Memory (ROM), a Random Access Memory (RAM), a Hardware Disk Drive (HDD), and an image memory, and peripheral circuitry such as a memory controller and a memory interface that are associated with these memories. As shown in FIG. 3, the storage 22 stores a two-dimensional image g_2d that is obtained by performing an X-ray imaging on a compressed breast 60 of a subject, and a plurality of pieces of tomographic images g_t1, g_t2, . . . , g_t49, g_t50 that are obtained by performing a tomosynthesis imaging on the compressed breast 60. In other words, the two-dimensional image g_2d and the tomosynthesis images g_tm are respectively imaged in a state where the positioning of the breast 60 is the same. Each of the plurality of pieces of tomographic images g_t1, g_t2, . . . , g_t49 and g_t50 may present a cross-sectional surface (a cross-sectional surface of a breast on the XY-plane) that is almost parallel to the two-dimensional image g_2d. The number of pieces of the tomographic image is not limited to 50 pieces; therefore, a plurality of pieces may be used. A group of the plurality of pieces of tomographic images g_t1, . . . , g_t50 may be referred a tomosynthesis image g_tm. The storage 22 may also associate and store, for example, a tomographic image number for identifying each of the tomographic images, a position of a pathological abnormality candidate, and a type of pathological abnormality. Here, for example, in the case where a position in direction Z of FIG. 2 indicates a tomographic image number, the position (x, y, r) of the pathological abnormality may be expressed by using a range of a radius r circle centering on a point (x,y) shown on an XY-coordinate within the tomographic image. The "position of a pathological abnormality candidate" may also be referred to as a "position of a region including a pathological abnormality candidate". The "region" here may be referred to as a "region of interest". Since a geometric state of the breast 60 in the two-dimensional image g_2d and the tomosynthesis image g_tm is the same, the position (x, y, r) of such pathological abnormality candidate may also be used in common in the two-dimensional image g_2d. Furthermore, in FIG. 3, although the two-dimensional image g_2d and the tomosynthesis image g_tm show the case in which a nipple 61 of the breast 60 is positioned on the right side, the position is not limited to this. Therefore, the direction of the image may be changed as needed. The storage 22 may also store a two-dimensional image g_2d-p to which image processing is applied. Furthermore, in FIG. 3, although the two-dimensional image g_2d-p shows an example of showing a calcification pathological abnormality candidate 62 and a tumor mass pathological abnormality candidate 63, it is not limited to this example. The storage 22 may also store the data of the two-dimensional image g_2d and the tomosynthesis image g_tm generated by the image generating circuit 25 in association with an imaging condition, a code indicating an imaging direction (imaging angle) upon imaging, and a code indicating a right or a left of the imaged breast.

The input interface 23 is realized by a trackball, a switch button, a mouse, a keyboard, a touch pad through which an input operation is performed by touching an operation surface, and a touch panel display, etc. with an integrated display screen and a touch pad, which are for an operator to input various commands, instructions, information, choices, and settings to the image processing apparatus 5. The input interface 23 is connected to the imaging control circuit 24 and the processing circuitry 26, etc., converts an input operation received from the operator into an electrical signal, and outputs the signal to the imaging control circuit 24 or the processing circuitry 26. Furthermore, in the present specification, the input interface 23 is not limited to only comprising physical operation members such as a mouse or a keyboard. As an example of the input interface 23, for example, electrical signal processing circuitry is included. The electrical signal processing circuitry receives an electrical signal corresponding to an input operation through an external input device provided separately from the apparatus, and outputs the electrical signal to the imaging control circuit 24 or the processing circuitry 26.

The interface 23 is an operation panel for setting an imaging condition (a tube voltage, a tube current-time lapse product, a material quality of an anode, a material quality of a radiation quality filter, a breast thickness, a distance between an X-ray focal point and an X-ray detector, and a magnifying ratio, etc.) for the imaging control circuit 24. The input interface 23 also sets a code indicating either the right or the left breast that is an imaging target for the imaging control circuit 24. The input interface 23 also comprises an interface for operating the C-arm 11. In accordance with an operation of such interface, the C-arm 11 is rotated about the Z-axis to be set to a given position. An imaging direction is decided in accordance with the position of the set C-arm 11.

The imaging control circuit 24 comprises an unillustrated processor and memory. The imaging control circuit 24 controls each structural element of the X-ray imaging apparatus 3 based on the imaging condition (a tube voltage, a tube current-time lapse product, a material quality of an anode, a material quality of a radiation quality filter, a breast thickness, a distance between an X-ray focal point and an X-ray detector, and a magnifying ratio, etc.) set via the input interface 23. In the above manner, the imaging control circuit 24 causes the X-ray imaging apparatus 3 to perform the X-ray imaging or the tomosynthesis imaging in accordance with the setting.

The image generating circuit 25 generates data of the two-dimensional image or the tomosynthesis image based on the digital signal from the imaging table 16. Usually, a vital region of an image obtained by the X-ray imaging or the tomosynthesis imaging includes not only a breast region, but also a region outside the breast region of a pectoralis major muscle region, etc.

Based on an instruction input by the operator via the input interface 23, the processing circuitry 26 reads out the two-dimensional image g_2d, a plurality of pieces of tomographic images g_t1, . . . , g_t50, the angle information, and a control program stored in the storage 22 and controls the image processing apparatus 5 accordingly. For example, the processing circuitry 26 is a processor that realizes each function for reducing the burden on the diagnostic reading doctor in accordance with the control program read out from the storage 22. Here, as examples of each function, there are a specifying function 26a, an image processing function 26b, and a display control function 26c, etc.

The specifying function 26a serves as a function to specify a position of the pathological abnormality candidate and the type of pathological abnormality of the breast from a plurality of pieces of tomographic images obtained by performing tomosynthesis imaging on the breast of a subject. For example, the specifying function 26a specifies the position of the pathological abnormality candidate and the type of pathological abnormality of the breast 60 by applying CAD to each of the plurality of pieces of tomographic images g_t1, . . . , g_t50. The specifying function 26a may also specify the position of the pathological abnormality candidate and the type of pathological abnormality of the breast 60 from each of the plurality of pieces of tomographic images g_t1, . . . , g_t50 in accordance with the operation of the input interface 23 by the diagnostic reading doctor while each of the tomographic images g_t1, . . . , g_t50 is being displayed. In other words, when specifying the position of the pathological abnormality candidate and the type of pathological abnormality, either the CAD or the diagnostic reading operation by the diagnostic reading doctor may be used.

The image processing function 26b serves as a function to apply image processing to a position corresponding to the specified position of the pathological abnormality candidate in the two-dimensional image g_2d in accordance with the pathological abnormality type. Here, the image processing function 26b may also perform image processing by adding, for example, an emphasizing component in accordance with the pathological abnormality type.

For example, in the case where the pathological abnormality type indicates a tumor mass, the image processing function 26b may add an emphasizing component of a low-frequency side. Here, the tumor mass is a mass inside the breast that consists of constituents slightly different from mammary glands or fat. Since the tumor mass of breast cancer and the mammary glands have X-ray absorption coefficients that are close to each other, they are indistinguishable from one another on the two dimensional image. In contrast, when the image processing for adding the emphasizing component of the low-frequency side to the two-dimensional image is performed, the tumor mass pathological abnormality candidate becomes easily-visible from the mammary glands. Furthermore, the tumor mass may be benign or malignant. Whether the tumor mass is benign or malignant may be determined by the shape, density, and margin (how it is rimmed), etc. of the tumor mass. In the case where the position of the pathological abnormality candidate indicating the pathological abnormality type as a tumor mass is shifted in each of the plurality of pieces of the tomographic images g_t, the image processing function 26b may perform the image processing on the two-dimensional image so as to apply a density difference between a center position of a group of each of the pathological abnormality candidate positions and a peripheral position surrounding the center position.

Furthermore, in the case where the pathological abnormality type indicates a calcification, the image processing function 26b may add an emphasizing component of a high-frequency side. Here, a calcification is what may be seen as a rock, resulting from a part of a blood vessel, a latex vessel, or a pathological abnormality transforming. The calcification may be benign or malignant. Whether the calcification is benign or malignant is determined based on the formation of the calcification or how the calcification is distributed inside the breast.

Furthermore, in the case where the pathological abnormality type indicates highly-dense mammary glands in the tomographic images of more than or equal to a predetermined number of pieces from among the tomographic images g_t1, . . . , g_t50, the image processing function 26b may determine the highly-dense mammary glands as a Focal Asymmetric Density (FAD), and apply image processing to the two-dimensional image in order to darken the position of the pathological abnormality candidate corresponding to the FAD. The "highly-dense mammary glands" may be read as "mammary glands having higher absorption than others". Here, the mammary gland is a tissue inside the breast. The breast mainly consists of mammary glands and fat. The "tomographic images of more than or equal to a predetermined number of pieces" may be read as "a number of tomographic images".

The display control function 26c serves as a function to control the display 27 to display the two-dimensional image g_2d-p to which the image processing has been applied.

The display 27 is comprised of a display main body that displays a medical image, etc. such as the two-dimensional image g_2d-p and the tomographic images g_t1, . . . , g_t50, an inner circuit that supplies a signal for display to the display main body, and peripheral circuitry such as a connector and cable for connecting the display main body and the inner circuit. The display 27 is controlled by the processing circuitry 26, and displays, for example, the two-dimensional image g_2d-p to which image processing has been applied by the processing circuitry 26.

The system control circuit 28 comprises an unillustrated processor and memory, and, as the nerve center of the X-ray diagnostic apparatus 1, controls each of the constituent elements.

The image processing apparatus 5 and the X-ray imaging apparatus 3 may be formed integrally. Furthermore, instead of this image processing apparatus 5, it may be modified to provide an image processing apparatus outside an unillustrated X-ray diagnostic apparatus. The image processing apparatus of a modified example stores a two-dimensional image and a plurality of pieces of tomographic images imaged by the X-ray diagnostic apparatus, and applies image processing to the two-dimensional image. The image processing apparatus of the modified example should only have the same function as at least the storage 22 and the processing circuitry 26, and does not need to have the same function as the aforementioned imaging control circuit 24, the image generating circuit 25, and the system control circuit 28. Furthermore, the image processing apparatus of the modified example may have a configuration that comprises the display 27, or may have a configuration that controls the display of an external display (display 27). Furthermore, the storage 22 and each of the functions 26a to 26c of the processing circuitry 26 in the image processing apparatus of the modified example execute almost the same operation as the storage 22 and each of the functions 26a to 26c of the processing circuitry 26 in the image processing apparatus 5 of the aforementioned X-ray diagnostic apparatus 1. Therefore, in the following explanation, a case in which the storage 22 and each of the functions 26a to 26c of the processing circuitry 26 exist in the image processing apparatus 5 of the X-ray diagnostic apparatus 1 is given as a representative example.

Now, the operation of the X-ray diagnostic apparatus configured in the above manner will be explained with reference to FIGS. 4 to 7. The following explanation will mainly be on an operation of the image processing after the X-ray imaging and the tomosynthesis imaging.

First of all, the X-ray diagnostic apparatus 1 receives a designation related to an imaging direction (MLO direction or CC direction) of the breast of the subject by the operation of a radiology technician. Here, it is assumed that, for example, the CC direction is designated.

Then, the X-ray diagnostic apparatus 1 reads input information that is input by an operator such as a radiology technician who operates the input interface 23, and adjusts the angle and height of the C-arm 11 in accordance with the imaging direction and the height of the breast.

Subsequently, the operator positions the breast of the subject on the X-ray imaging apparatus 3. When performing positioning for the X-ray imaging, the breast is held between the compression plate 17*a* and the imaging surface (imaging table 16). The compression plate 17*a* is then lowered or brought closer. After the compression plate 17*a* is lowered or brought closer, when needed, the operator's hand is placed between the compression plate 17*a* and the breast to flatten the breast by the operator's hand so that the mammary glands are in a spread out state. In order to maintain this state, at the same time as when the operator withdraws his/her hand, the breast is fixed by the compression plate 17*a*. In this manner, the positioning of the X-ray imaging is completed.

Subsequently, the X-ray imaging is performed on the breast in the above fixed state. An X-ray is irradiated on the breast by the operation of the input interface 23 by the operator. Here, an X-ray corresponding to a condition of a predetermined X-ray irradiation dose, etc. is irradiated towards the breast. A digital detector of the imaging table 16 detects the X-ray transmitted through the breast. In the case where the digital detector in the imaging table 16 is an FPD, the detected X-ray is converted into an electrical signal. The electrical signal is output to the image processing apparatus 5 as a digital signal via the amplifier circuit and the A/D conversion circuit. The image generating circuit 25 generates a two-dimensional image g_g2 based on the digital signal.

Figure 4:
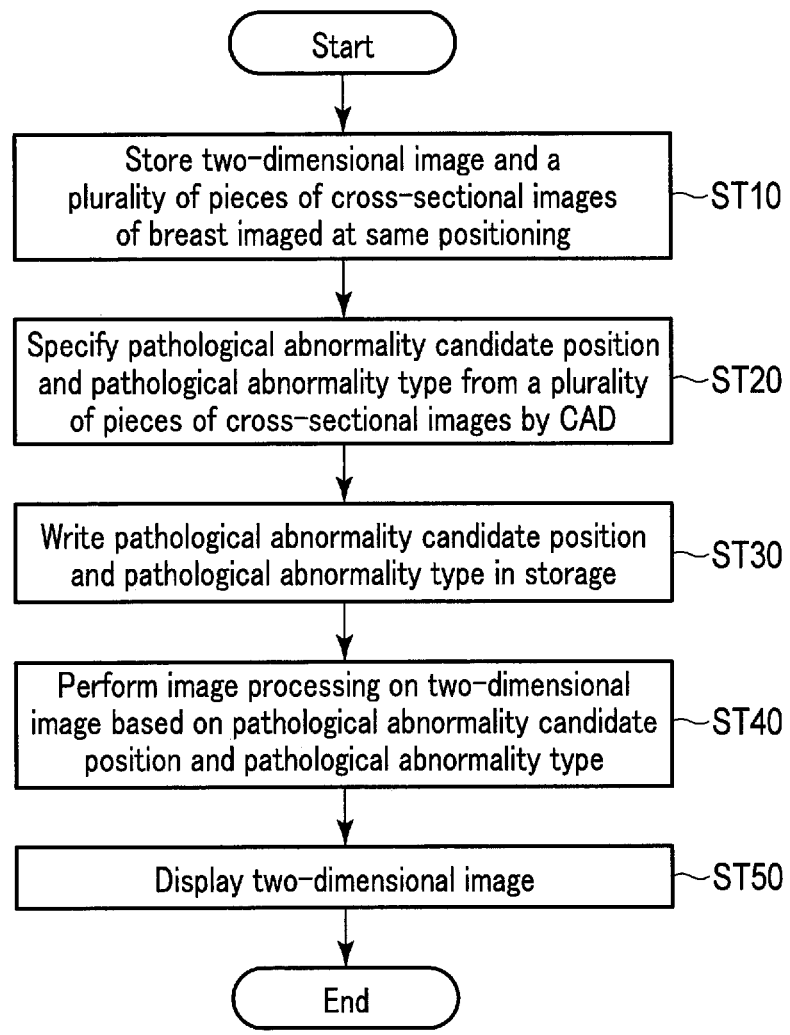
FIG. 4 is a flowchart for explaining an operation of the present embodiment.

In step ST10, as shown in FIG. 4, in the X-ray diagnostic apparatus 1, the two-dimensional image g_g2 obtained by performing X-ray imaging on the breast of the subject is stored in the storage 22 by the image generating circuit 25. Furthermore, in the X-ray diagnostic apparatus 1, the tomosynthesis imaging is performed on the breast in the same positioning as the breast upon this X-ray imaging, to obtain a plurality of pieces of tomographic images g_t1, g_t2, . . . , g_t49 and g_t50. The obtained plurality of pieces of tomographic images g_t1, . . . , g_t2, g_t49 and g_t50 are stored in the storage 22 by the image generating circuit 25. In the case of performing imaging of the breast of the subject from a different imaging direction, or performing imaging of the other breast after the tomosynthesis imaging is performed, a series of processing is repeated again, and, when all of the imaging is completed, the imaging is ended. After the imaging is ended, in the operation thereafter the next step ST20, instead of the X-ray diagnostic apparatus 1 being operated by the operator, for example, the image processing apparatus 5 is operated by the diagnostic reading doctor. However, the operation does not have to be limited to this. Therefore, for example, the operator may continue operating the image processing apparatus 5, and the diagnostic reading doctor may perform diagnostic reading on the two-dimensional image, etc. displayed by the image processing apparatus 5. In any case, after step ST10 is ended, the procedure moves on to step ST20.

In step ST20, in the image processing apparatus 5 of the X-ray diagnostic apparatus 1, the specifying function 26*a* of the processing circuitry 26 performs the CAD on each of the plurality of pieces of tomographic images g_t1, . . . , g_t50, and specifies the position of the pathological abnormality candidate and the pathological abnormality type of the breast 60. For example, as shown in FIG. 5, assume that the specifying function 26*a* specifies the position (x1, y1, r1) of the pathological abnormality candidate and the pathological abnormality type "calcification" of the breast 60 as a result of performing the CAD on the tomographic image g_t20. Similarly, assume that the specifying function 26*a* specifies the position (x2, y2, r2) of the pathological abnormality candidate and the pathological abnormality type "tumor mass" of the breast 60 as a result of performing the CAD on the tomographic image g_t30. At such time, assume that the specifying function 26*a* specifies the positions (x3, y3, r3), . . . , (x13, y13, r13) of the pathological abnormality candidate and the pathological abnormality type "FAD" of the breast 60 as a result of performing the CAD on the unillustrated tomographic images g_t35, . . . , g_45.

In step ST30, the specifying function 26*a* writes the specified results of step ST20 in the storage 22. In this manner, the storage 22 stores the position of the pathological abnormality candidate and the pathological abnormality type of the breast 60.

In step ST40, the image processing function 26*b* of the processing circuitry 26 performs image processing on the two-dimensional image g_2d within the storage 22 based on the position of the pathological abnormality candidate and the pathological abnormality type within the storage 22. In other words, the image processing function 26*b* performs image processing on the position of the pathological abnormality candidate in the two-dimensional image g_2d in accordance with the pathological abnormality type. For example, the image processing function 26*b* performs image processing to add an emphasizing component of the low-frequency side in the case where the pathological abnormality type indicates a tumor mass, and performs image processing to add an emphasizing component of the high-frequency side in the case where the pathological abnormality type indicates calcification. In the two-dimensional image g_2d_p to which the image processing has been applied, for example, as shown in FIG. 5, a calcification pathological abnormality candidate 62 and a tumor mass pathological abnormality candidate 63 are emphasized, respectively.

Figure 6:
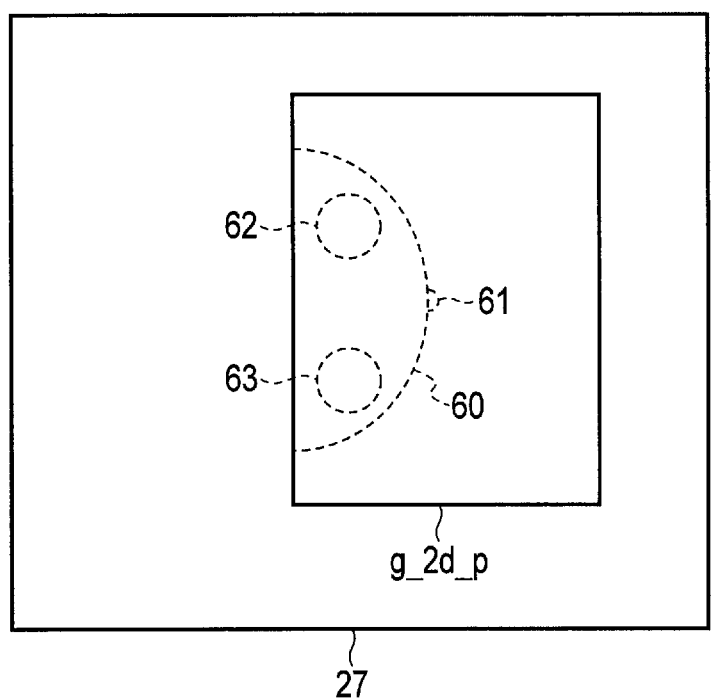
FIG. 6 is a schematic view for explaining an operation of the present embodiment.

In step ST50, the display control function 26*c* of the processing circuitry 26 controls the display 27 to display the two-dimensional image g_2d-p to which the image processing has been applied. As shown in FIG. 6, for example, the display 27 displays the two-dimensional image g_2d-p that brightly expresses each of the calcification pathological abnormality candidate 62 and the tumor mass pathological abnormality candidate 63.

This allows the diagnostic reading doctor to easily observe, for example, the calcification pathological abnormality candidate 62 and the tumor mass pathological abnormality candidate 63 when diagnostically reading the two-dimensional image g_2d-p, to which the image processing has been applied.

Figure 7:
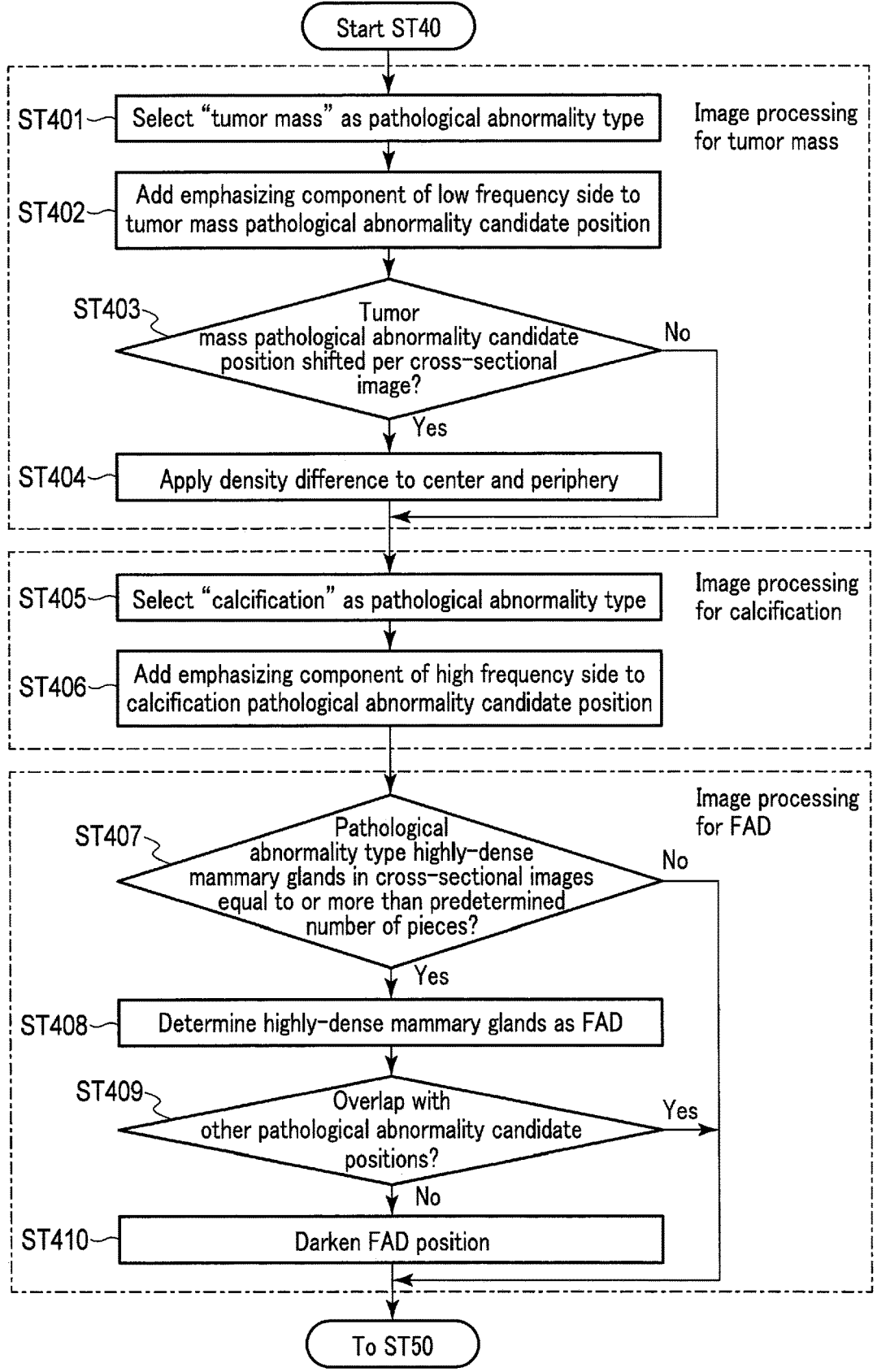
FIG. 7 is a flowchart for explaining a part of the operation of the present embodiment in detail.

Next, the operation of the image processing according to the aforementioned step ST40 will be explained in detail with reference to FIG. 7. In the following, the image processing for the tumor mass (ST401 to ST404), the image processing for the calcification (ST405 to ST406), and the image processing for the Focal Asymmetric Density (FAD) (ST407 to ST410) will be explained in order. The order of each of the image processing may be switched as needed.

However, in the case where a position to which image processing for the tumor mass or the calcification is to be applied overlaps with a position to which image processing for the FAD is to be applied, the image processing for the tumor mass or the calcification will be prioritized. Furthermore, among the image processing for the tumor mass, the image processing (ST403 to ST404) for the tumor mass pathological abnormality candidate that has thickness may be omitted. In any case, in the following explanation, as shown in FIG. 7, a case in which the image processing is executed in the order of the tumor mass, the calcification, and the FAD is given as a representative example.

First of all, in steps ST401 to ST402, the image processing function 26*b* selects the pathological abnormality type "tumor mass" as the image processing target, and performs image processing on a position of the tumor mass pathological abnormality candidate 63 in the two-dimensional image g_2d to add an emphasizing component of the low-frequency side. In the two-dimensional image g_2d_p on which the image processing has been performed, the tumor mass pathological abnormality candidate 63 is shown emphasized.

In step ST403, the image processing function 26*b* determines whether or not the position of the pathological abnormality candidate whose pathological abnormality type is indicated as the "tumor mass" is shifted in each of the plurality of pieces of tomographic images g_t. As a result of the determination, in the case where the position is not shifted, the processing moves on to step ST405, and in the case where the position is shifted, the processing moves on to step ST404.

In step ST404, in the case where each of the positions of the tumor mass pathological abnormality candidate 63 is shifted, the image processing function 26*b* performs image processing on the two-dimensional image g_2d-p so as to apply a difference in density between a center position of a group of each position of the tumor mass pathological abnormality candidates 63 and a peripheral position surrounding the center position. The image processing function 26*b* then ends the image processing for the tumor mass and moves on to step ST405.

In steps ST405 to ST406, the image processing function 26*b* selects the pathological abnormality type "calcification" as the image processing target, and performs image processing on a position of the calcification pathological abnormality candidate 62 in the two-dimensional image g_2d to add an emphasizing component of the high-frequency side. In the two-dimensional image g_2d_p on which the image processing has been performed, the calcification pathological abnormality candidate 62 is shown emphasized. In the above manner, the image processing function 26*b* ends the image processing for the calcification and moves on to step ST407.

In steps ST407 to ST408, the image processing function 26*b* determines whether or not the pathological abnormality type indicates highly-dense mammary glands in the tomographic images of more than or equal to a predetermined number of pieces among the plurality of pieces of tomographic images g_t1, . . . , g_t50. As a result of the determination, in the case where the highly-dense mammary glands are not indicated, the processing is ended and moves on to step ST50. In the case where the highly-dense mammary glands are indicated, the highly-dense mammary glands are determined as the Focal Asymmetric Density (FAD), and, after the pathological abnormality type is rewritten from the "highly-dense mammary glands" to the "FAD" in the storage 22, the processing moves on to step ST409. The highly-dense mammary glands do not necessarily have to be determined as the FAD. Similarly, the highly-dense mammary glands do not necessarily have to be rewritten into the FAD. However, in such case, the "FAD" in steps ST409 to ST410 should be read as the "highly-dense mammary glands".

In step ST409, the image processing function 26*b* determines whether or not the position of the FAD overlaps with the positions of the other pathological abnormalities. As a result of the determination, in the case where the positions overlap, the processing ends and moves on to step ST50. In the case where the positions do not overlap, the processing moves on to step ST410.

In step ST410, the image processing function 26*b* performs image processing to darken the position of the pathological abnormality candidate corresponding to the FAD. In the above manner, the image processing function 26*b* ends the image processing for the FAD and moves on to step ST50.

In the following, step ST50 is executed in the same manner as mentioned above.

As mentioned above, according to the embodiment, the position of the pathological abnormality candidate and the pathological abnormality type of the breast is specified from a plurality of pieces of tomographic images obtained by performing tomosynthesis imaging on the breast of a subject. In the two-dimensional image obtained by performing X-ray imaging on the breast, the image processing is performed on a position corresponding to the position of the specified pathological abnormality candidate in accordance with the pathological abnormality type.

Therefore, by the above-mentioned image processing, a two-dimensional image that allows easy observation when being displayed on a display can be obtained, which would reduce the burden on the diagnostic reading doctor. In the case of the U.S. breast cancer examination work flow, when specifying the position of the pathological abnormality candidate and the pathological abnormality type, a diagnostic reading operation of a diagnostic reading doctor (A) at the image center, or the CAD will be used. In the case of using the diagnostic reading operation of the diagnostic reading doctor (A), the burden on a diagnostic reading doctor (B) who is a family doctor of the subject will be reduced. In the case of using the CAD, the diagnostic reading doctor (A) would not have to perform diagnostic reading, for confirmation, on the two-dimensional image to which the image processing has been applied in accordance with the result of specification by the CAD. In any case, in the case of using the CAD, a burden on both of the diagnostic reading doctors (A) and (B) will be reduced. Even in cases other than the U.S. breast cancer examination work flow, the above explanations may be similarly applied by replacing and reading the "diagnostic reading doctor (A) at the image center" as an "expert diagnostic reading doctor (A)".

To supplement the explanation, a plurality of pieces of tomographic images that are obtained by performing tomosynthesis imaging on the breast at the same positioning as that upon performing imaging of the two-dimensional image will be read through CAD. When a pathological abnormality candidate is detected from one of the tomographic images, the position of the pathological abnormality candidate and the pathological abnormality type are stored. Furthermore, when applying image processing to the two-dimensional image, first, a usual image processing is performed, then, additionally, the image processing is applied to only the pathological abnormality candidate position in accordance with the pathological abnormality type.

Here, since the amount of information included in the two-dimensional image to which the image processing has been applied is greater than the conventional two-dimensional image, the two-dimensional image displayed on the display would be easily observed, and the pathological abnormality candidate would be easily viewed, through which improvement in the diagnostic performance can be expected. Furthermore, by applying the image processing regarding the pathological abnormality candidate to the two-dimensional image, improvement in throughput of diagnostic reading and reduction in the possibility of missing a breast cancer can be expected. In addition to this, since diagnostic reading should be performed only on a piece of a two-dimensional image to which information regarding the pathological abnormality candidate is added from the tomographic images obtained by performing the tomosynthesis imaging, the burden on the diagnostic reading doctor can be reduced in comparison to the conventional case in which diagnostic reading is performed on all of the tomographic images or a plurality of the tomographic images. Therefore, as mentioned above, a two-dimensional image that allows easy observation when being displayed on a display can be obtained, which would reduce the burden on the diagnostic reading doctor.

Furthermore, the processing circuitry used in the embodiment may also perform image processing by adding an emphasizing component in accordance with the pathological abnormality type. In this case, each pathological abnormality candidate having pathological abnormality types different from each other can be easily observed on the two-dimensional image.

Furthermore, in the case where the pathological abnormality type indicates a tumor mass, the processing circuitry may add an emphasizing component of a low-frequency side. In this case, the tumor mass pathological abnormality candidate can be easily observed on the two-dimensional image. Here, in the case where the position of the pathological abnormality candidate indicating a tumor mass as the pathological abnormality type shifts in each of a plurality of pieces of the tomographic images, a hard thick pathological abnormality candidate is imaged. Therefore, in the case where each of the pathological abnormality candidate positions indicating the pathological abnormality type as a tumor mass is shifted, the image processing may be performed on the two-dimensional image so that a density difference is applied between a center position of a group of each pathological abnormality candidate position and a peripheral position surrounding the center position. In this case, a thick hard tumor mass pathological abnormality candidate can be easily observed on the two-dimensional image.

Furthermore, in the case where the pathological abnormality type indicates calcification, the processing circuitry may add an emphasizing component of a high-frequency side. In this case, the calcification pathological abnormality candidate can be easily observed on the two-dimensional image.

Furthermore, in the case where the pathological abnormality type indicates highly-dense mammary glands in tomographic images of more than or equal to a predetermined number of pieces from among several tomographic images, the processing circuitry may determine the highly-dense mammary glands as a Focal Asymmetric Density (FAD), and apply image processing to the two-dimensional image in order to darken a position corresponding to the position of the pathological abnormality candidate corresponding to the FAD. In this case, since a white region corresponding to the position of the FAD is darkened on the two-dimensional image, the region corresponding to the position of the FAD can be easily observed. To supplement the explanation, in the prior arts, in either case of the two-dimensional image displayed on the display or the two-dimensional image formed on a film, a tumor mass inside the highly-dense mammary glands was difficult to be distinguished from a white region corresponding to the FAD position. In contrast, according to the embodiment, since the white region corresponding to the FAD position is darkened, a region corresponding to the FAD position can be easily observed.

Furthermore, each of a plurality of pieces of tomographic images may also display a cross-sectional surface that is approximately parallel to the two-dimensional image. In this case, the position of the pathological abnormality candidate inside each of the tomographic images and the position of the pathological abnormality candidate inside the two-dimensional image can be easily corresponded. Accordingly, in comparison to the case in which each of a plurality of pieces of tomographic images does not express a cross-sectional surface that is approximately parallel to the two-dimensional image (for example, in the case of expressing a cross-sectional surface that is approximately perpendicular to the two-dimensional image), a burden on the image processing function 26b can be reduced.

Modified Example

Now, a modified example of the embodiment will be explained. In this example, portions that overlap with the embodiment will not be explained, and mainly those portions that are different will be mentioned.

In this modified example, in addition to displaying a two-dimensional image, a configuration that switches and displays the tomographic images used to perform specification in step ST20 is presented.

Specifically, for example, in addition to the aforementioned functions, the display control function 26c of the processing circuitry 26 has a function of displaying a display switch button of the tomographic images, and controlling a display so that the tomographic images are displayed or not displayed in accordance with the operation of the display switch button.

The other configurations are the same as the aforementioned embodiment.

Figure 8:
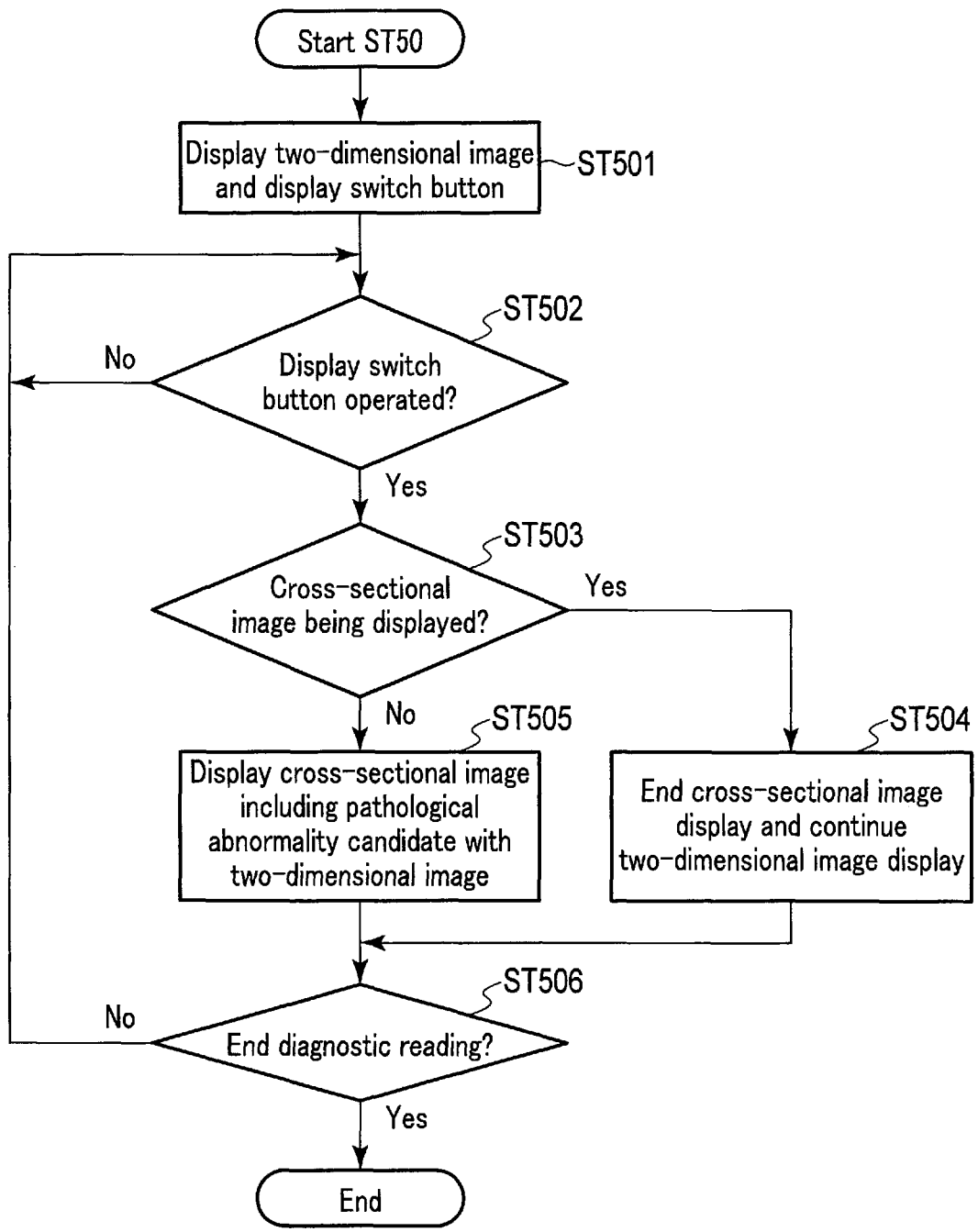
FIG. 8 is a flowchart for explaining an operation of a modified example of the present embodiment.
Figure 9:
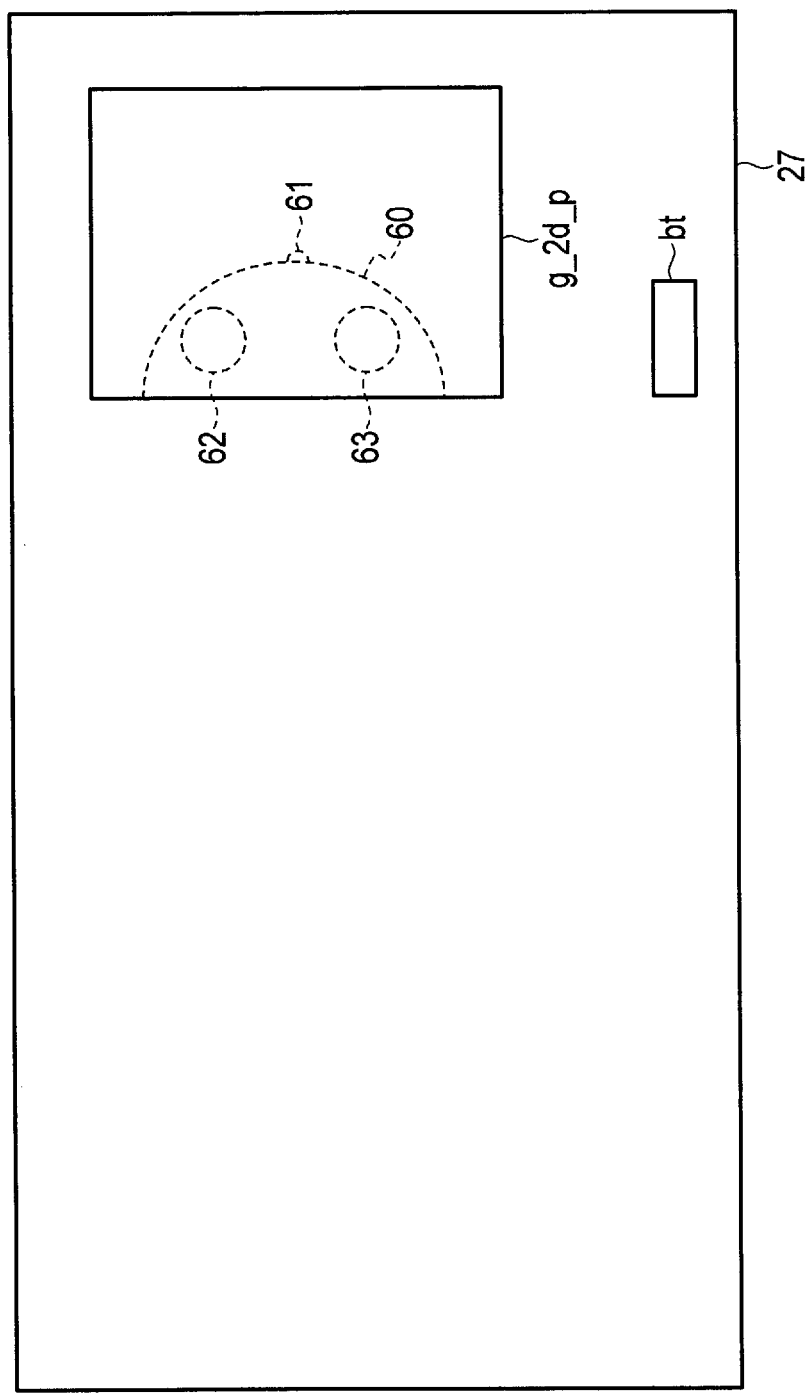
FIG. 9 is a schematic view for explaining an operation of the modified example of the present embodiment.

According to the modified example configured in the above manner, the aforementioned step ST50 is executed in the manner shown, for example, in steps ST501 to ST506 of FIG. 8.

In step ST501, as shown in FIG. 8, the display control function 26c controls a display 27 so that a two-dimensional image g_2d-p to which image processing is applied, and a display switch button bt are displayed. The display 27 displays, for example, a two-dimensional image g_2d-p on which a calcification pathological abnormality candidate 62 and a tumor mass pathological abnormality candidate 63 are emphasized, and the display switch button bt. A display layout of these two-dimensional images g_2d-p and display switch button bt can be set as appropriate.

In step ST502, the display control function 26c determines whether or not the display switch button bt has been operated. In the case where it has not been operated, step ST502 is repeatedly executed. In the case where the display switch button bt has been operated, the processing moves on to step ST503.

In step ST503, the display control function 26c determines whether or not a tomographic image is being displayed. In the case where it is displayed, the processing moves on to step ST504. In the case where it is not displayed, the processing moves on to step S505.

In step ST504, the display control function 26c ends displaying the tomographic image, and continues displaying the two-dimensional image g_2d-p. Subsequently, the display control function 26c moves on to step ST506.

Figure 10:
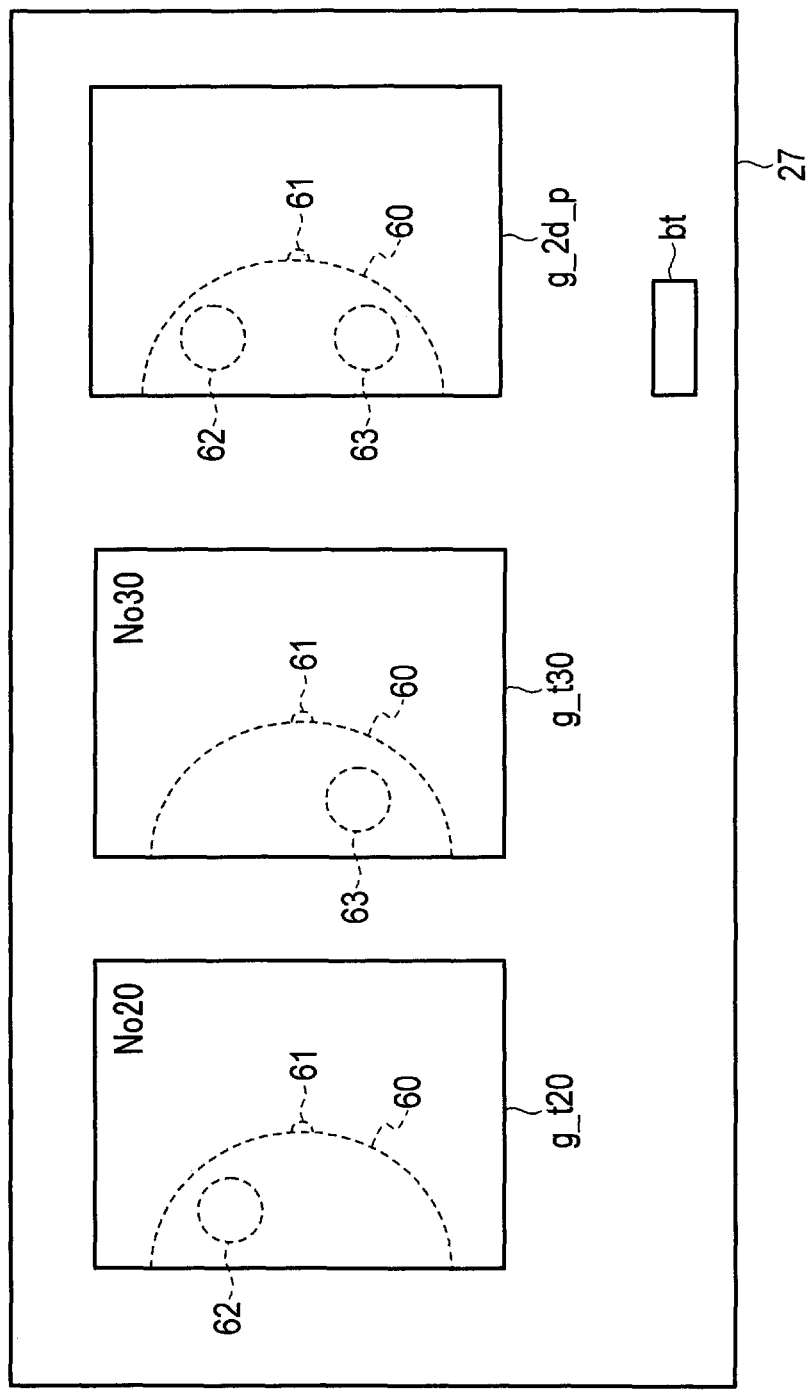
FIG. 10 is a schematic view for explaining an operation of the modified example of the present embodiment.

In step ST505, as shown in FIG. 10, the display control function 26c controls the display 27 in a manner that tomographic images g_t20 and g_t30 including pathological abnormality candidates are displayed together with the two-dimensional image g_2d-p based on tomographic image numbers inside a storage 22. The display layout of the tomographic images g_t20 and g_t30, the two-dimensional image g_2d-p, and the display switch button bt can be set as appropriate. Here, each of the tomographic images g_t20 and g_t30 may be displayed together with a neighboring predetermined number of pieces of tomographic images. For example, the tomographic image g_t20 may be displayed together with tomographic images g_t17 to g_t19 and g_t20 to g_t23, and the tomographic image g_t30 may be displayed together with tomographic images g_t27 to g_t29 and g_t31 to g_t33. In this case, since a diagnostic reading doctor is also able to observe the adjacent tomographic images in addition to the tomographic images g_t20 and g_t30 used for specifying pathological abnormality candidates, improvement in diagnostic performance can be expected. In any case, after step ST505, the display control function 26c moves on to step STS06.

In step STS06, for example, the display control function 26c determines whether or not the diagnostic reading is ended according to whether or not an unillustrated diagnostic reading end button has been operated, and ends the processing if the diagnostic reading is ended. In the case where the diagnostic reading is not ended, the processing returns to step ST502, and the processing is continued.

According to the above modified example, in the case where the diagnostic reading doctor wishes to observe the tomographic images g_t20 and g_t30 used for the image processing of the two-dimensional image g_2d-p, the tomographic images g_t20 and g_t30 are displayed on the display 27. Accordingly, in addition to the effect of the embodiment, the tomographic image used for specifying the pathological abnormality candidate can be easily observed.

To supplement the explanation, in the modified example, since the diagnostic reading is performed on the tomographic images g_t20 and g_t30 used for specifying the pathological abnormality candidate, the number of pieces of images to perform diagnostic reading increases from the embodiment. Nevertheless, the burden on the diagnostic reading doctor in the modified example has been significantly reduced in comparison to the conventional case in which diagnostic reading was performed on all of the tomographic images. Accordingly, also in the modified example, the two-dimensional images displayed on the display can be easily observed in the same manner as in the embodiment, which would reduce the burden on the diagnostic reading doctor. In addition to this, according to the modified example, since the tomographic images g_t20 and g_t30 used for specifying the pathological abnormality candidate are displayed in accordance with the operation of the display switch button bt, the required tomographic images g_t20 and g_t30 can be easily observed without causing the diagnostic reading doctor to go through the trouble of searching for the tomographic images.

The term "processor" used in the above explanation indicates, for example, a circuit, such as a CPU (central processing unit), a GPU (Graphics Processing Unit), or an Application Specific Integrated Circuit (ASIC), and a programmable logic device (for example, a Simple Programmable Logic Device (SPLD), a Complex Programmable Logic Device (CPLD), and a Field Programmable Gate Array (FPGA)). The processor realizes its function by reading and executing the program stored in the storage. Instead of storing the program in the storage, the program may be directly integrated into the circuit of the processor. In this case, the processor realizes the function by reading and executing the program integrated into the circuit. Each processor of the present embodiment is not limited to a case in which it is configured as a single circuit. Therefore, a plurality of independent circuits may be combined to configure a processor to realize the function thereof. Furthermore, a plurality of constituent elements shown in FIG. 1 may be integrated into a processor to realize the function thereof.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

The invention claimed is:

1. An X-ray diagnostic apparatus comprising processing circuitry configured to:
    specify a position of a pathological abnormality candidate and a pathological abnormality type of a breast of a subject from a plurality of pieces of tomographic images obtained by performing tomosynthesis imaging on the breast;
    in a two-dimensional image obtained by performing X-ray imaging on the breast, perform image processing on a position corresponding to the position of the specified pathological abnormality candidate in accordance with the pathological abnormality type;
    control a display to display the two-dimensional image on which the image processing is performed and a display switch button of the tomographic images; and
    control the display to display or not display the tomographic images used to specify the position of the specified pathological abnormality candidate in accordance with an operation of the display switch button.

2. The X-ray diagnostic apparatus according to claim 1, wherein the processing circuitry is configured to apply computer-aided detection (CAD) to each of a plurality of pieces of the tomographic images to specify the position of the pathological abnormality candidate and the pathological abnormality type.

3. The X-ray diagnostic apparatus according to claim 1, wherein the processing circuitry is configured to perform the image processing by adding an emphasizing component in accordance with the pathological abnormality type.

4. The X-ray diagnostic apparatus according to claim 3, wherein, in a case where the pathological abnormality type is a tumor mass, the processing circuitry is configured to add an emphasizing component of a low-frequency side.

5. The X-ray diagnostic apparatus according to claim 4, wherein, in a case where the position of the pathological abnormality candidate with the pathological abnormality type indicated as the tumor mass is shifted in each of the plurality of pieces of tomographic images, the processing circuitry is configured to perform the image processing on the two-dimensional image to apply a density difference between a center position of a group of positions of the pathological abnormality candidate and a peripheral position surrounding the center position.

6. The X-ray diagnostic apparatus according to claim 3, wherein, in a case where the pathological abnormality type indicates calcification, the processing circuitry is configured to add an emphasizing component of a high-frequency side.

7. The X-ray diagnostic apparatus according to claim 1, wherein, in a case where the pathological abnormality type indicates highly-dense mammary glands in tomographic images equal to or more than a predetermined number of pieces among a plurality of pieces of the tomographic images, the processing circuitry is configured to determine the highly-dense mammary glands as a Focal Asymmetric Density (FAD), and perform the image processing on the two-dimensional image so as to darken a position corresponding to the position of the pathological abnormality candidate corresponding to the FAD.

8. An image processing apparatus comprising processing circuitry configured to:
specify a position of a pathological abnormality candidate and a pathological abnormality type of a breast of a subject from a plurality of pieces of tomographic images obtained by performing tomosynthesis imaging on the breast;
in a two-dimensional image obtained by performing X-ray imaging on the breast, perform image processing on a position corresponding to the position of the specified pathological abnormality candidate in accordance with the pathological abnormality type;
control a display to display the two-dimensional image on which the image processing is performed and a display switch button of the tomographic images; and
control the display to display or not display the tomographic images used to specify the position of the specified pathological abnormality candidate in accordance with an operation of the display switch button.

9. The image processing apparatus according to claim 8, wherein the processing circuitry is configured to apply computer-aided detection (CAD) to each of a plurality of pieces of the tomographic images to specify the position of the pathological abnormality candidate and the pathological abnormality type.

10. The image processing apparatus according to claim 8, wherein the processing circuitry is configured to perform the image processing by adding an emphasizing component in accordance with the pathological abnormality type.

11. The image processing apparatus according to claim 10, wherein, in a case where the pathological abnormality type is a tumor mass, the processing circuitry is configured to add an emphasizing component of a low-frequency side.

12. The image processing apparatus according to claim 11, wherein, in a case where the position of the pathological abnormality candidate with the pathological abnormality type indicated as the tumor mass is shifted in each of the plurality of pieces of tomographic images, the processing circuitry is configured to perform the image processing on the two-dimensional image to apply a density difference between a center position of a group of positions of the pathological abnormality candidate and a peripheral position surrounding the center position.

13. The image processing apparatus according to claim 10, wherein, in a case where the pathological abnormality type indicates calcification, the processing circuitry is configured to add an emphasizing component of a high-frequency side.

14. The image processing apparatus according to claim 8, wherein, in a case where the pathological abnormality type indicates highly-dense mammary glands in tomographic images equal to or more than a predetermined number of pieces among a plurality of pieces of the tomographic images, the processing circuitry is configured to determine the highly-dense mammary glands as a Focal Asymmetric Density (FAD), and perform the image processing on the two-dimensional image so as to darken a position corresponding to the position of the pathological abnormality candidate corresponding to the FAD.

* * * * *